United States Patent [19]

Wallace

[11] Patent Number: 5,342,316
[45] Date of Patent: Aug. 30, 1994

[54] RESEALABLE SAMPLING PORT

[76] Inventor: Henry G. Wallace, Whitehall Road, Colchester, essex CO2 8JH, United Kingdom

[21] Appl. No.: 107,906

[22] Filed: Aug. 17, 1993

Related U.S. Application Data

[63] Continuation of Ser. No. 834,467, Feb. 12, 1992, abandoned.

[30] Foreign Application Priority Data

Feb. 14, 1991 [GB] United Kingdom ............... 9103122
Jul. 3, 1991 [GB] United Kingdom ............... 9114341

[51] Int. Cl.⁵ ..................... A61M 5/00; A61M 31/00
[52] U.S. Cl. ......................... 604/167; 604/201; 604/256; 604/278; 604/905; 251/149.1; 137/845
[58] Field of Search ............ 604/167, 169, 201, 237, 604/244, 256, 278, 905; 137/845; 251/149.1

[56] References Cited

U.S. PATENT DOCUMENTS

| 4,000,739 | 1/1977 | Stevens | 604/167 X |
|---|---|---|---|
| 4,303,069 | 12/1981 | Cohen | 604/201 |
| 4,781,693 | 11/1988 | Martinez et al. | 604/244 X |
| 5,000,745 | 3/1991 | Guest et al. | 604/167 X |
| 5,102,395 | 4/1992 | Cheer et al. | 604/167 |

OTHER PUBLICATIONS

WO89/06553, Baxter, *Pre-Slit Injection Site and Tapered Cannula* Jul. 1989.
Patent Specification 1,444,210, Gizard & Boyer *Stoppers for Closing Containers* Jul. 1976.

*Primary Examiner*—Randall L. Green
*Assistant Examiner*—Mary Beth Jones
*Attorney, Agent, or Firm*—Woodcock Washburn Kurtz Mackiewicz & Norris

[57] ABSTRACT

The invention relates to a resealable port (2), or an injection site (24), for use with a syringe cone (16), the port being formed with a housing including a conduit (1) sealed by a resealable diaphragm (7) wherein a sealing annulus (6) is juxtaposed to, and interacts with, the diaphragm (7) to form an annulus and diaphragm assembly whereby the arrangement of the housing and the assembly is such that action of the syringe cone (16) as it passes through the diaphragm generates a cantilever action about a point (12) which serves to seal the diaphragm and the annulus in the housing.

12 Claims, 3 Drawing Sheets

RESEALABLE SAMPLING PORT

This is a continuation of application Ser. No. 07/834,467, filed Feb. 12, 1992, now abandoned.

The present invention relates to resealable sampling ports and injection sites, particularly for biological materials. Sampling ports and injection sites can be used to extract or deliver a fluid from, or to, a conduit without introducing microorganisms into the conduit and without allowing the contents of the conduit to leak after a syringe has been withdrawn. The port or site may be swabbable either by being flush with the housing or by being accessible in a reasonable manner for example by cotton wool. Swabbing is necessary to disinfect the external surface of the diaphragm to prevent contamination of the conduit contents and also to stop growth of bacteria in residual fluid resulting from extraction of a sample of the conduit contents.

Such arrangements are known to be provided with a resealable diaphragm which may optionally be pre-slit. Whereas resealable diaphragms are satisfactory for use with a needle, since the puncture in the resealable septum or diaphragm is small, there are problems associated with utilising a syringe having a cone for introduction through a pre-slit resealable diaphragm since the external bore of the cone is much larger than that of the needle and presents a challenge to the resealability of the diaphragm.

It is obviously desirable to use syringes for sampling where possible because their use avoids the problem of needlestick and because syringes can remove and deliver much greater quantities of liquid more rapidly than needles. Further, the cost of replacement needles is saved, and the problem of needle disposal is reduced.

Conical resealing valves for cooperation with Luer-type syringes are known in the art. One such example was made by Rusch in Germany in 1967 and comprised a resealable septum in a bore which was adapted to accommodate the syringes. Such devices are more suitable where the septum does not require to be disinfected for example by swabbing. Also they cannot prevent flash-back of fluid into a pre-entry portion of the valve. Foley urological catheters, commonly have a pre-slit diaphragm to accept a Luer syringe cone.

WO89/06553 (Baxter) provides a shaped pre-slit resealable bung retained in an annular recess coaxial therewith. The recess is a precise fit in the radial direction and is provided with an annular space into which bung material may be forced as the syringe cone slides through the slit in use. Since the syringe cone has a taper increasing force upon the syringe acts to progressively deform the bung during interengagement. However, the design of the bung is such that the arrangement cannot be used with a standard Luer taper due to the inbuilt radial compression exerted on the diaphragm by the housing assembly. Thus a special adaptor cannula must be fitted to the syringe before engagement with the bung. This arrangement thus relies upon radial deformation of the bung into the annular space to open and reseal repeatedly. The arrangement as shown in Baxter is therefore unsuited to smaller sampling ports, and even with pre-slit injection sites requires a relatively high interengagement pressure. One of the problems with the withdrawal of blood by a needle or syringe cone has been that blood tends to be left, after withdrawal of the needle or syringe cone on the housing or exterior of the needle or cone.

This has been addressed in Baxter WO89-06553 by swabbing the top of the septum and the cone as appropriate and with this in mind the target area of the septum is convex. Another approach to this problem has been in discussed in GB-A-1444210 which provides a bung with a bore terminating in a resealable septum and being provided with an inwardly directed annulus adapted to contact the needle to wipe the blood from the exterior faces thereof. In an embodiment of the present invention this is improved by the use of (a) an arrangement for ensuring that the withdrawal of the cone temporarily increase the wiping pressure; and (b) by providing a double wiping action.

One object of the present invention is thus to provide an annulus and diaphragm assembly for cooperation with a housing of a sampling port or injection site, which assembly allows for the easy introduction of a syringe cone, while ensuring a good biological seal between the cone and the assembly. A further object is to provide an annulus and diaphragm assembly wherein a cantilever action is used to apply a point loading against the exterior of the cone as it is either introduced or withdrawn from the injection site or sampling port.

Another object is to provide an injection site incorporating a double cantilever effect for sealing purposes which is particularly, although not exclusively, suited to an injection site.

Another object for the invention is to provide a sampling port, or injection site, in which sealing can be effected between the cone and the annulus and diaphragm assembly without the undue pressure and deformation of the diaphragm previously required.

Another object of the invention is to provide an annulus an diaphragm assembly which in its at-rest condition forms a laterally slidable seal within the housing of a port or injectable site, which seal is reinforced by cantilever action between the housing and the assembly on introduction, and optionally withdrawal, of a syringe cone.

Accordingly rather than cause a radial deformation of the septum as required in the Baxter disclosure, the present invention provides in essence means whereby a cantilever action is employed to seal the diaphragm assembly while the syringe cone is introduced and to reseal the said assembly as the cone is removed.

Sealing against the syringe cone is achieved at least in part by a cantilever action of the diaphragm on entry of the cone. This approach makes possible a light and compact port and/or an effective injection site.

Accordingly specifically therefore to the present invention there is provided in first aspect a resealable port for use with a syringe, terminating in a blunt syringe cone, said port being formed by a housing including a conduit sealed by a resealable diaphragm; characterized in that a sealing annulus is juxtaposed to, and interacts with, the diaphragm to form an annulus and diaphragm assembly, and in that the arrangement of the housing and the diaphragm is such that the action of a syringe cone as it passes into the diaphragm generates a cantilever action which serves to seal the diaphragm and annulus in the housing and against the cone.

In a further aspect of the invention there is provided a resealable diaphragm and sealing annulus assembly formed of a biologically acceptable resilient material and comprising a generally planar portion to form the diaphragm having a pre-slit channel disposed generally centrally thereof; and coaxial of said channel an upstanding or downwardly depending sealing annulus, said annulus having a bore approximating to the external dimensions of a syringe cone with which it is to be used; said diaphragm being capable of flexing about the pre-slit channel to urge the adjacent portion of the sealing annulus into abutment with the cone in use. Preferably the syringe cone in accordance with the present invention has a defined taper and may for example be a standard Luer syringe cone having a 6% taper. The material to be withdrawn, sampled or introduced, is most preferably a biological material such as blood or urine; or a biologically active agent such as for example insulin.

The resealable diaphragm should be capable of a slight centering action if possible relative to the housing to accommodate inaccuracy in locating the syringe cone in the diaphragm.

In a preferred form of the invention the annulus and the diaphragm are integrally formed. In such an arrangement the peripheral portions of the integral annulus and diaphragm units may be provided with a central channel thereby to define outwardly directed portions. The annulus and diaphragm are preferably loosely retained by the housing perpendicular to the axis of entry of the cone, thereby to accommodate an eccentric cone. It is also preferred that the opening of a sampling port should be in the form of a bowl or well having a diameter less than that of the diaphragm to provide a cantilever point.

In a preferred form of the invention the diaphragm is pre-slit and the annulus has an at-rest diameter slightly less than that of a coaxial bore in a retaining cap. By this means the act of passing the syringe cannula through the bore in the cap until said syringe is in contact therewith, also seals the annulus against the syringe cone; which seal is reinforced by the action of the diaphragm on the sealing annulus.

In such an arrangement it will preferably be arranged that the displacement of annulus on interengagement of the syringe cone with the annulus also serves to seal the annulus and the diaphragm against the housing and the retaining cap.

The invention will now be described, by way of illustration only, with reference to the accompanying drawings wherein.

Figure 2:
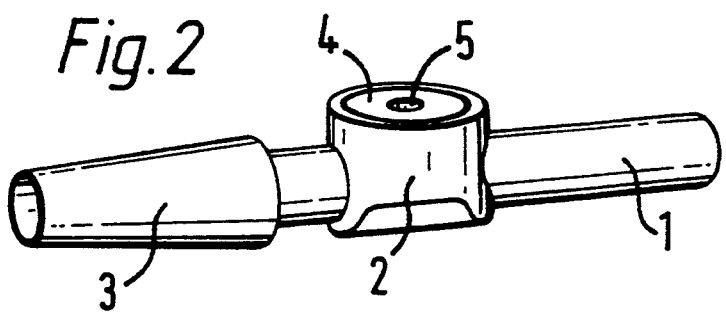
FIG. 2 shows a side view from above of the port as shown in FIG. 1.

With reference first to FIG. 2 a cylindrical bore defining a conduit 1 is provided at its remote end with a connector portion 3 of standard type. Disposed about the conduit 1 is a generally annular sampling port 2, provided on its upper face with a retaining cap 4 provided with a retaining cap bore 5 adapted in use to accommodate a Luer syringe cone (16).

Figure 1:
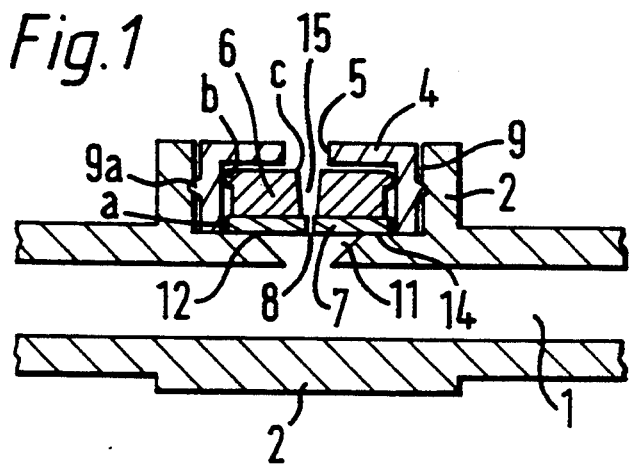
FIG. 1 shows a vertical cross section through a sampling port in accordance to the present invention.

Turning now to FIG. 1. The conduit 1 is provided on its upper face with an upstanding portion forming the sampling port 2. The inner face of the sampling port 2 is provided with a channel 9. The circular floor of the sampling port 2 is depressed to form a well 11 which forms a generally bow shape in cross-section so as to provide a connection through into the conduit 1. The well 11 terminates at a cantilever point 12. The floor 14 extends radially outwardly from the point 12 towards the inner periphery of the sampling port 2.

The sampling port 2 also accommodates a coaxial retaining cap 4 provided on its outer face with a rib 9a for cooperation with channel 9 to lock the said cap into the port 2. Alternatively, the retaining cap may be welded or bonded in situ. The retaining cap 4 is provided with a retaining cap bore 5 which is generally coaxial about the well 11. Retained in the space formed by the retaining cap 4 and the floor 14 is a diaphragm and annular seal assembly, wherein the diaphragm is designated 7 and the annular seal designated 6. It will be noted that the annular seal 6 is provided with an internal blind bore 15 terminating at its lower most end in the diaphragm 7. The diaphragm 7 is provided with a pre-slit channel 8. It will be appreciated that in its normal at-rest condition the annular seal and diaphragm assembly is a firm sliding seal between the lower face of the retaining cap 4 and the floor 14. A strong pressure exerted on a side of the annular seal 6 will allow a slight lateral movement of the assembly to a limited extent, as in the normal at-rest condition there is a firm seal between the conduit and the exterior.

Figure 3:
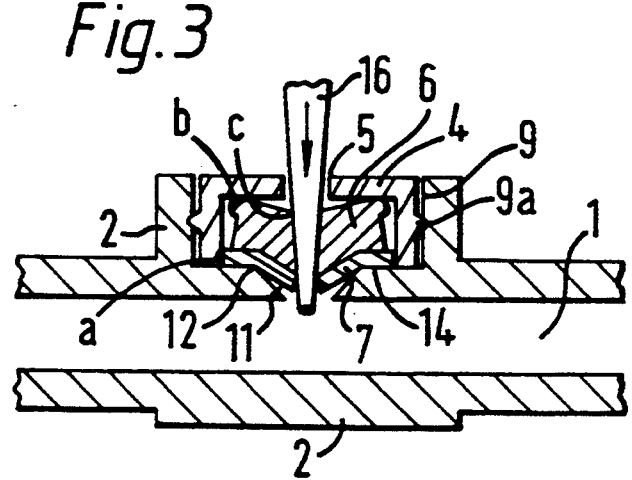
FIG. 3 shows a side view of the FIG. 1 in use.

In use as shown in FIG. 3 a cone of a Luer syringe 16 is passed through the bore 5 and into the annular seal 6. Since such a Luer cone has a 6% taper initially it will pass through the annular seal 6 with a minimum deformation. Further urging of the cone towards to the conduit 1 causes the tip of the cone to enter the pre-slit channel 8 and deform the diaphragm downwardly into the well 11. At the same time the extra penetration causes the outer periphery of the cone to come into contact with the edges of the retaining cap bore 5.

The effect of this arrangement is to force the center of the diaphragm downwardly about the cantilever point 12. Because of the bulk of the cone, the diaphragm is distended outwardly in a radial direction whereby the point (a) is forced into compression with the inner face of the wall of the retaining cap. Further, the cantilever moment about the point 12 forces the point (b) of the annular seal into compression against the underside of the retaining cap 4, while because of the geometry of the bore in the annular seal a point (c) is forced more firmly against the wall of the cone.

Because the annular seal and the diaphragm are formed of a biologically acceptable resilient material such as natural rubber, the cone when fully introduced is locked into the sampling port by means of its contact with the bore 5 in the retaining cap 4, the point (c) of the annular seal and because it is distended through the pre-slit channel 8. In this condition biological materials flowing in the conduit 1 can be extracted or additional components added to the said conduit as desired.

Withdrawal of the cone from the pre-slit channel 8 allows the assembly to return to its at-rest condition as shown in FIG. 1 without allowing any leakage and without any collateral damage to the diaphragm 7 itself.

When the tip of the cone 16 has been sampling blood, for example, it is desirable that as much blood as possible is removed from the cone as the cone exits the sampling port. This arrangement achieves this with facility. As cone 16 is withdrawn, the diaphragm 7 is urged upwardly until the upper face of the annulus 6 abuts the underside of the cap 4. At this point the cone is relatively withdrawn from the annulus and diaphragm assembly. Because of the shape of the bore in the annulus sliding contact between the cone and the annulus is not only maintained but is also slightly increased as the cone is withdrawn. Thus blood is wiped off the cone and particularly from the tip thereof as it passes through the diaphragm and annulus assembly, in part at least because of this "reverse cantilever" action.

It will be appreciated that in the arrangement as shown the diaphragm and the annular seal are made of the same material and are integral. However, a device can equally well be made where the annular seal and the diaphragm are made of different biologically acceptable forms of material and are separate; said separation may be physical, or may be via an adhesive layer if appropriate.

Figure 3A:
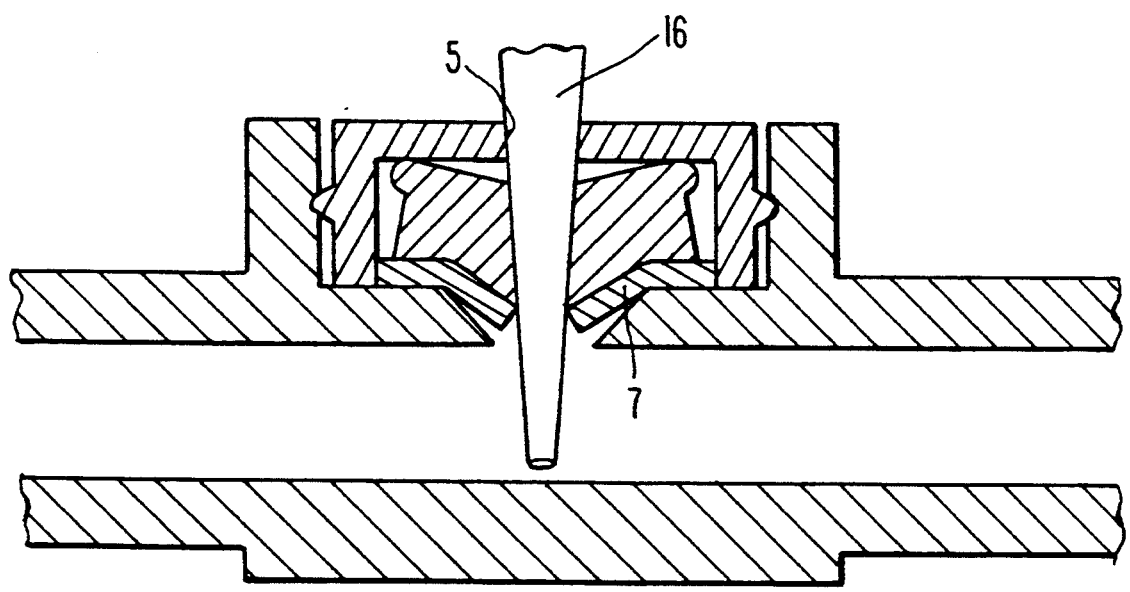
FIG. 3a depicts the view of FIG. 3 showing the relationship of cone 16 and bore 5.

FIG. 3a depicts the preferred size relationship of cone 16 and bore 5. The cone is preferably of a larger width than that of the bore.

FIGS. 4 to 7 relate to different forms of an injectable site. In FIGS. 4 to 7 injection sites formed with a female Luer lock screw thread are shown. A male Luer lock screw thread can be substituted.

Figure 4:
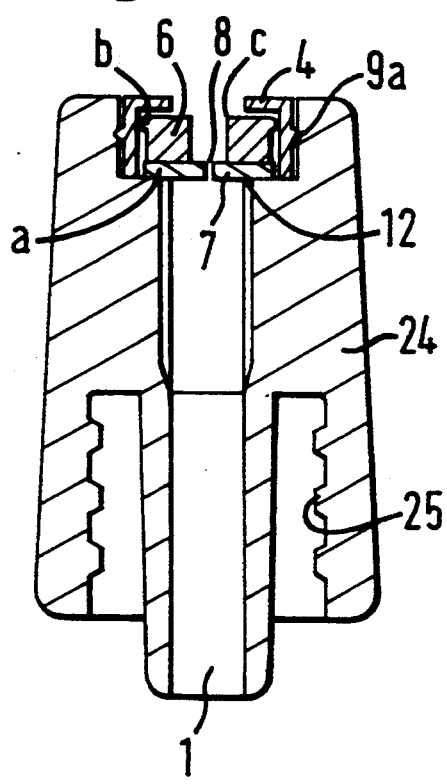
FIG. 4 shows in vertical cross-section the arrangement of FIG. 1 applied to an injection site.

With specific reference to FIG. 4 there is provided an annular seal 6 and a resealable diaphragm 7 substantially as shown in FIG. 1 and which operates substantially in accord with the arrangement shown in FIG. 3. This modus operandi has been already described with reference to FIG. 3 and will not be described further with the exception that it will be noted that the conduit 1 is coaxial with the annular seal and resealable diaphragm assembly rather than disposed perpendicular thereto. The housing 24 is formed with a cantilever point 12 substantially as shown in FIG. 1. The housing 24 is also provided with coaxial Luer screw threads 25 of known type.

While the arrangement of FIG. 4 works satisfactorily it presents a problem that the surface of the diaphragm 7 is not readily swabbable for the purposes of sterilization. Accordingly, in the arrangement shown in FIG. 5 the annular seal 6 and the resealable diaphragm 7 are reversed such that the resealable diaphragm 20 is positioned superior to the lower sealing annulus 20. It will be noted that the introduction of a cone 16 into the resealable diaphragm 20 causes a cantilever action of the diaphragm and a deformation of the annulus outwardly.

Figure 5:
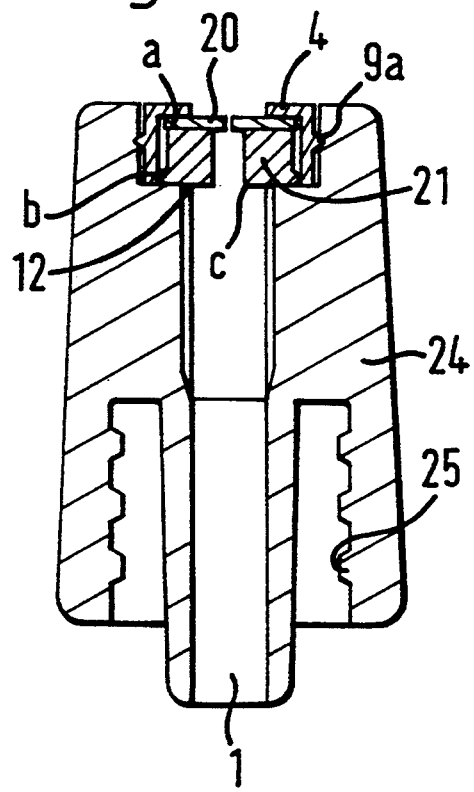
FIG. 5 shows a vertical cross-section of another form of diaphragm and annulus assembly of FIG. 4.
Figure 6:
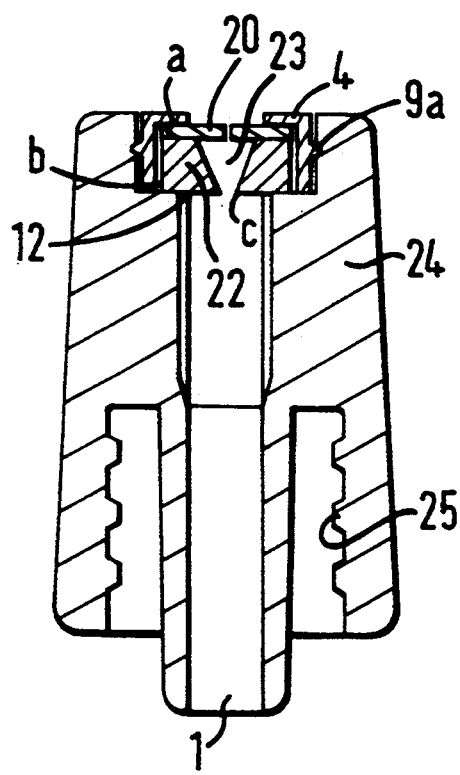
FIG. 6 shows in vertical cross-section a further form of diaphragm and annulus assembly.
Figure 7:
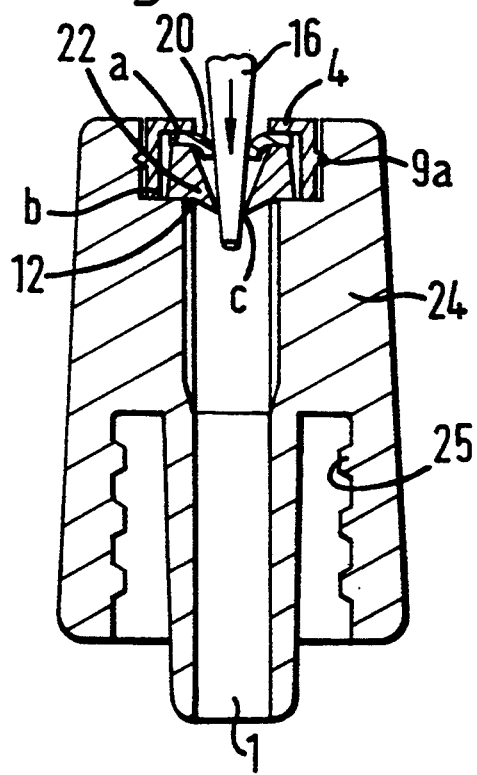
FIG. 7 shows in vertical cross-section an arrangement of FIG. 6 in use with a syringe cone.

The arrangement of FIG. 6 presents an improvement of the arrangement of FIG. 5 in that the annular seal 22 is formed with a fusto-conical space 23. This arrangement, shown operational detail in FIG. 7, provides for a double seal against the cone of the syringe 16 as it is introduced into the injectable site. On withdrawal of the cone 16 the initial action is to increase the sealing pressure between the diaphragm 20 and the annular seal 22 before a sliding action is engendered. The double seal as shown in FIG. 7 is particular useful in preventing contaminants from being left on the cone after withdrawal.

By use of the present arrangement it has been found that a large number of introductions of a Luer cone of standard dimensions can be accommodated without degrading the natural rubber diaphragm and allowing organism entry. The invention therefore provides a novel resealable sampling port and/or an injection site and a combined resealable diaphragm and sealing annulus for use therewith. Further the retaining cap provides a bore to lock the taper of a syringe cone when the cone is fully inserted into the port when the device is utilised for a resealable sampling port.

I claim:

1. A resealable sampling port and sealing assembly for use with a syringe terminating in a blunt syringe cone, said port being formed with a housing including a conduit sealed by said sealing assembly comprising a resealable diaphragm and a sealing annulus, said assembly being retained in a portion of the housing defining a centrally disposed chamber of a first diameter and wherein the assembly is retained in said housing by a retaining cap; characterized in that the sealing annulus has a diameter less than the first diameter, thereby creating an annular space between the sealing annulus and the chamber, and forming a laterally slidable seal within said annular space, such that the action of a syringe cone as it passes into the assembly within the housing generates a cantilever action of the assembly against the housing and thus against the cap portion which serves to seal the sealing assembly within the housing.

2. A port according to claim 1 wherein the resealable diaphragm is disposed between the sealing annulus and the retaining cap.

3. A port according to claim 1 wherein the sealing annulus is disposed between the resealable diaphragm and the retaining cap.

4. A port according to claim 1 wherein the sealing annulus comprises a frusto-conical central opening such that withdrawal of the cone from the diaphragm exerts an increased pressure between the cone, and the assembly to seal the same against the withdrawing cone.

5. A sampling port according to claim 1 wherein the sealing annulus and resealable diaphragm are integral and are provided with a rib portion extending radially therefrom along a minor portion of an axial dimension thereof, wherein said rib portion contacts the retaining cap.

6. A sampling port according to claim 1 wherein the diaphragm is pre-slit.

7. A sampling port according to claim 1 wherein the retaining cap further comprises an axial bore of a diameter less than the maximum diameter of the blunt syringe cone.

8. A sealing assembly sealing a resealable sampling port for use with a syringe, the sealing assembly mounted in a housing having a chamber of a first diameter, said sealing assembly comprising:
 a resealable diaphragm; and
 a sealing annulus retained in said housing between a retaining cap and the diaphragm, and within said chamber,
 wherein the sealing assembly has a diameter less than the first diameter, thereby defining an annular space between the assembly and the chamber, and forming a laterally slidable and expandable seal,
 whereby when the syringe passes into the assembly a cantilever action of the sealing annulus against the diaphragm, the housing and the retaining cap seals the resealable sampling port.

9. The resealable cap of claim 8, wherein the retaining cap defines an inlet port and the resealable diaphragm is disposed adjacent the inlet port.

10. The resealable cap of claim 8, wherein the retaining cap defines an inlet port and the sealing annulus is disposed adjacent the inlet port.

11. The resealable cap of claim 8, further comprising a centrally located frustoconical opening in the resealable diaphragm.

12. The resealable cap of claim 8, wherein the resealable diaphragm defines an outer surface and an axial dimension, and further comprising a radially extending rib portion having an axial dimension that is a minor portion of the axial dimension of the resealable diaphragm, whereby the rib portion acts as a pivot for said cantilever action.

* * * * *